United States Patent [19]

Abrutyn et al.

[11] Patent Number: 5,409,695

[45] Date of Patent: Apr. 25, 1995

[54] METHOD OF INCREASING DEPOSITION OF SILICONE CONDITIONER TO HAIR

[75] Inventors: Eric S. Abrutyn; Marjorie F. Dwane, both of Midland, Mich.

[73] Assignee: Dow Corning Corporation, Midland, Mich.

[21] Appl. No.: 199,434

[22] Filed: Feb. 22, 1994

[51] Int. Cl.6 .......................... A61K 9/16; A61K 7/075
[52] U.S. Cl. .................................. 424/70.12; 424/401; 424/489; 424/70.121
[58] Field of Search .................... 424/70, 71, 401, 487, 424/489, 78.03

[56] References Cited

U.S. PATENT DOCUMENTS

| | | | |
|---|---|---|---|
| 4,724,240 | 2/1988 | Abrutyn | 514/847 |
| 4,962,133 | 10/1990 | Chromecek | 521/56 |
| 5,034,218 | 7/1991 | Duvel | 424/70 |
| 5,034,220 | 7/1991 | Helioff | 424/73 |
| 5,085,857 | 2/1992 | Reid | 424/70 |
| 5,156,914 | 10/1992 | Shih | 428/402.22 |
| 5,208,038 | 5/1993 | Gressani | 424/489 |

Primary Examiner—Thurman K. Page
Assistant Examiner—Sally Gardner
Attorney, Agent, or Firm—James L. DeCesare

[57] ABSTRACT

A method of increasing the deposition of a silicone conditioner to hair. The silicone conditioner is delivered to the hair in an aqueous shampoo and is a polydimethylsiloxane fluid entrapped in a nontoxic hydrophobic macroporous highly crosslinked polymer. The macroporous polymer is a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns.

2 Claims, No Drawings

METHOD OF INCREASING DEPOSITION OF SILICONE CONDITIONER TO HAIR

BACKGROUND OF THE INVENTION

This invention is directed to hair conditioning and to the enhancement in deposition of a conditioner to the hair.

Unless hair is washed with an extremely weak shampoo or very infrequently, it is necessary to return some oil to the hair to "condition" it. Conditioning is typically equated with good combing properties, body, curl retention, the elimination of "fly-away", enhanced luster, and improved feel.

In a fast-paced society, hair can undergo significant damage due to humidity, temperature, exposure to sunlight, frequent washing, combing, and brushing, as well as cosmetic treatments such as bleaching, dyeing, and waving. The retention of oil on the hair can alleviate to some extent the damage.

Therefore, the problem to be solved by the present invention is to increase the amount of oil which can be deposited on hair when it is conditioned, in order to prevent some of the abuse which the hair undergoes in a modern society.

This problem is solved, according to the invention, by delivering a conditioning oil to the hair which is a polysiloxane fluid, most preferably with a viscosity of at least sixty thousand centistokes, entrapped in a nontoxic hydrophobic macroporous highly crosslinked polymer.

SUMMARY OF THE INVENTION

The invention relates to a method of increasing the deposition of a silicone conditioner to hair. According to the invention, the silicone conditioner is delivered to the hair as an ingredient of an aqueous shampoo. The shampoo contains an anionic surfactant and a nonionic surfactant. The silicone conditioner is a polysiloxane fluid most preferably with a viscosity of at least sixty thousand centistokes. The silicone conditioner is entrapped as an active ingredient in a nontoxic hydrophobic macroporous highly crosslinked polymer.

It has been found that if the macroporous polymer is in the form of a mixture of particulates including (i) unit particles having an average diameter of less than one micron; (ii) agglomerates formed of fused unit particles and having an average diameter of about twenty to eighty microns; and (iii) aggregates formed of clusters of fused agglomerates and having an average diameter of two-hundred to twelve-hundred microns; that deposition of the particular silicone conditioner on the hair can be significantly improved.

These and other features, objects, and advantages, of the present invention will become more apparent from a consideration of the following detailed description thereof.

DETAILED DESCRIPTION OF THE INVENTION

The silicone conditioner according to the present invention is "entrapped" within particles of a hydrophobic macroporous highly crosslinked polymethacrylate polymer or copolymer. These particles are hydrophobic and not water soluble or water swellable. Such macroporous polymethacrylate materials can be manufactured in the form of spherical beads, plugs, and in the form of a complex particulate consisting of unit particles, agglomerates and aggregates.

The hydrophobic polymeric material used to entrap the silicone conditioning agent in the method of the present invention is macroporous, due to its complex arrangement of unit particles, agglomerates and aggregates. As a result of this complex structure, the material possesses an inordinate amount of interstitial space, including a vast labyrinth of voids. Volatile ingredients entrapped within the void volume of the material, are released by wicking to the surface, and evaporate at a rate dependent upon temperature, vapor pressure and surface area. Nonvolatile ingredients migrate to the surface by means of capillary action, and can be released on contact with another surface. Mechanical disruption may be used to release an entrapped ingredient.

While the material is shear sensitive, it is not compression sensitive. The material is capable of wicking ingredients from another surface in a sponge-like manner. The material does not shrink or expand, and is capable of adsorbing several times its own weight of an active ingredient. Since the process involved is adsorption in contrast to absorption, the properties of both the polymeric material and the active ingredient are not altered.

Active ingredients are entrapped within the material in contrast to being encapsulated. Encapsulation connotes a complete enclosing of one material within another, such as a shell formed around a core of liquid. Encapsulated ingredients are released by mechanical disruption of the shell or dissolution of the shell, and once the shell is disrupted, the entire contents of the shell are extracted. In entrapment, however, the release of the entrapped ingredient is controlled or sustained by wicking, evaporation and capillary action, and no mechanical disruption is required. Thus, the active ingredient is permitted a relatively unobstructed ingress and egress into and out of the labyrinth of voids of the crosslinked hydrophobic macroporous polymer.

The discrete particles of the hydrophobic macroporous material of the present invention are capable of entrapping solids and liquids, and are free flowing particulates, even when loaded with an active ingredient. One polymer which is representative of the materials in accordance with the present invention has the formula:

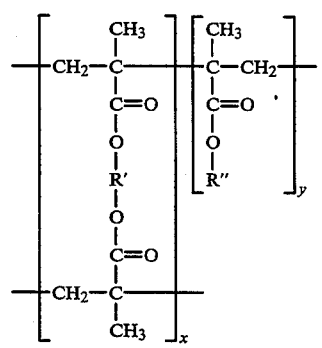

wherein x and y are integers in which the ratio of x:y is from 1:99 to 99:1; R' is an alkylene radical of the formula $(-CH_2CH_2-)_a$ in which a is an integer having a value of from one to eight; and R" is an alkyl group of the formula $-(CH_2)_bCH_3$ in which b has a value of from zero to twenty-nine. Preferably, the ratio of x to y is 80:20, R' is —$CH_2CH_2$— and R" is —$(CH_2)_{11}CH_3$.

This hydrophobic polymeric material is a highly crosslinked polymethacrylate. It is a low density, highly porous, free-flowing, white particulate. The particles are capable of adsorbing high levels of lipophilic liquids, while at the same time maintaining a free-flowing particulate character. The polymer can be formed by polymerizing a single polyunsaturated monomer such as ethylene glycol dimethacrylate or tetraethylene glycol dimethacrylate. The polymer may also be formed by polymerizing two monomers, at least one of which is a polyunsaturated monomer, with a monounsaturated monomer such as lauryl methacrylate or 2-ethylhexyl methacrylate.

Depending upon the process for making the material, the polymer can be produced in the form of (i) a bead having an average diameter of about ten microns to about one hundred-fifty microns; (ii) a plug having a diameter of 45000 microns and a length of 15000 microns; or (iii) a mixed powdered particulate which consists of unit particles, aggregates and agglomerates.

The particulate (iii) is in the form of a mixture of three different types of particles. The mixture includes unit particles of less than one micron in average diameter, agglomerates of fused unit particles of twenty to eighty microns in average diameter, and aggregates of clusters of fused agglomerates of two hundred to twelve hundred microns in average diameter. Whether the polymer is in the form of a spherical macroporous bead, a plug, or in the form of the complex mixture of particles, the structure will entrap various active ingredients.

Precipitation polymerization which employs an anhydrous hydrocarbon solvent, is the preferred method for producing the hydrophobic macroporous crosslinked polymer particulate form (iii) of the present invention. In this process, there is polymerized one monounsaturated monomer and one polyunsaturated monomer, in the presence of an excess of a volatile organic liquid, which is a solvent for the monomers and the initiator but not a solvent for the polymer. Polymerization of the monomers is initiated by means of a free radical generating catalytic compound which precipitates the polymer in the solvent in the form of a mixed structure which includes unit particles, aggregates and agglomerates. A dry particulate mixture is formed by removing the volatile hydrocarbon solvent from the precipitated polymeric particulate, leaving behind a structured submicron sized adsorbent material.

Hydrocarbon solvents which may be employed are (i) saturated aliphatic hydrocarbons such as cyclohexane, hexane, and heptane; (ii) aromatic hydrocarbons such as benzene, toluene and xylene; and (iii) aliphatic alcohols such as ethanol, isopropyl alcohol and butyl alcohol. The most preferred solvent is isopropyl alcohol.

The monounsaturated monomer and the polyunsaturated monomer can be present in varying mole ratios such as 20:80, 30:70, 40:60 or 50:50. The process includes the step of stirring the monomers, the solvent, and the free radical generating catalytic compound during polymerization. The particulate is dried by filtering excess solvent from the particulate and vacuum drying. The particulate may be used in its dry empty form in some end use applications, or it can be specially formulated by "post adsorbing" the empty particulate with various functional active ingredients.

Adsorption of active ingredients into the polymeric matrix is achieved by using a stainless steel mixing bowl and a spoon. The active ingredient is simply added to the empty dry particulate in the bowl, and the spoon is used to gently fold the active ingredient into the particulate. Low viscosity fluids may be adsorbed by addition of the fluids to a sealable vessel containing the particulate, and tumbling the materials until the desired consistency is achieved. More elaborate blending equipment such as ribbon or twin cone blenders can also be employed.

The following example illustrates the method of making an adsorbent particulate mixture by precipitation polymerization in an anhydrous hydrocarbon solvent.

EXAMPLE I

Into a five hundred milliliter reactor equipped with a paddle type stirrer was added 13.63 grams of ethylene glycol dimethacrylate monomer (eighty mole percent), and 4.37 grams of lauryl methacrylate monomer (twenty mole percent). To the reactor was added 282 grams of isopropyl alcohol as the hydrocarbon solvent, and 0.36 grams of benzoyl peroxide as the catalytic initiator. The monomers and the initiator are soluble in the hydrocarbon solvent but not the polymer which precipitates. The mixture including the monomers, the hydrocarbon solvent, and the catalytic initiator was purged with nitrogen. The system was heated in a water bath to about sixty degrees Centigrade until polymerization was initiated, and the temperature was increased to seventy-five degrees for six hours to complete polymerization. During the interval, the polymer precipitated from the anhydrous hydrocarbon solution. The polymerization produced unit particles of a diameter less than one micron. Some of the unit particles adhered and fused together, forming agglomerates of twenty to eighty microns in diameter. Some agglomerates adhered and fused together to form aggregates of loosely held assemblies of the agglomerates of two hundred to twelve hundred microns in diameter. The mixture was filtered to remove excess solvent, and a wet particulate cake was tray dried in a vacuum oven. A dry hydrophobic polymeric mixture of particulates consisting of unit particles, agglomerates and aggregates was isolated.

The method of Example I is representative of precipitation polymerization in which the monomers and the initiator are dissolved in a compatible anhydrous hydrocarbon solvent in which the monomers and initiator will solubilize. The hydrocarbon is a nonsolvent for the polymer, and hence a polymer in the form of a particulate will be precipitated.

In contrast to emulsion and suspension polymerization, no surfactant or dispersing aid is required to stabilize the particles. The materials produced are randomly shaped particles in contrast to the spherical beads obtained in suspension polymerization.

The particulate of Example I is unique in its ability to adsorb liquids and yet remain free flowing. The material provides a regulated release of ingredients which are entrapped and therefore it has the capability of functioning as a carrier. The particulate will disappear when rubbed upon a surface. This phenomenon is due to the fact that the large aggregates scatter light and provide the appearance of a white particulate, but when rubbed, these shear sensitive large aggregates are decreased in size approaching the range of visible light and seem to disappear.

The following example illustrates a bulk polymerization process in which an organic ester is entrapped "in situ" in the polymer. This system is anhydrous and no hydrocarbon solvent is employed. The ester remains entrapped according to this example. This method is used to produce large plugs.

EXAMPLE II

Seven grams of 2-ethylhexyl oxystearate ester was mixed with 1.5 grams of ethylene glycol dimethacrylate and 1.5 grams of lauryl methacrylate in a glass test tube. The solution was deaerated for five minutes and 0.1 milliliters of t-butyl peroctoate was added and mixed while heating to eighty degrees Centigrade in an oil bath. After twenty minutes, the contents of the glass test tube solidified and the mixture was maintained at the same temperature for an additional hour to assure full polymerization. A white heterogeneous bulk polymer resulted containing the entrapped ester.

The product of Example I differs from the product of Example II in that a volatile hydrocarbon solvent is used in Example I, and the solvent is removed resulting in a dry empty particulate material which is free of active ingredients. In Example II, a non-volatile functional material is bulk polymerized "in situ" but the active ingredient remains entrapped in the product. In addition, the form of the product in Example II is a bulk form or plug which fills its container, whereas in Example I the product is particulate.

In contrast to both Examples I and II, suspension polymerization is another technique in which polymerization is carried out in water. The monomers, active ingredient, and the catalyst are combined, and form beads or droplets in water and polymerization occurs within each bead. A surfactant or stabilizer (such as polyvinyl pyrrolidone) is required to prevent individually formed beads and droplets from coalescing. The resulting beads with the active material entrapped have a substantially spherical outer crust or shell but an interior macroporous structure. The bead is typically about ten to one hundred-fifty microns in average diameter depending upon the rate of agitation employed during the process.

Example III illustrates a process for the production of spherical beads by suspension polymerization in which an organic ester is entrapped "in situ" within the beads.

EXAMPLE III

Into a two liter three necked flask equipped with a stirrer, thermometer, and a nitrogen purge, there was added 1.2 grams of polyvinyl pyrrolidone dissolved in 1500 milliliters of water. A solution of 335 grams of 2-ethylhexyl oxystearate ester, 132 grams of ethylene glycol dimethacrylate, 33 grams of 2-ethylhexyl methacrylate, and five milliliters of t-butyl peroctoate was bubbled with nitrogen for five minutes. This mixture was slowly added to the stirred aqueous solution of polyvinyl pyrrolidone at twenty-two degrees Centigrade under nitrogen purge. The temperature was raised to eighty degrees with constant agitation and maintained for fifteen minutes until polymerization initiated. The temperature was maintained at eighty degrees for an additional two hours to complete the reaction. White beads were collected by filtering away supernatant liquid and the beads were dried to remove excess water. The beads had an average diameter of 0.25 to 0.5 millimeters.

Other stabilizers and protective colloids such as starch, polyvinyl alcohol, carboxymethyl cellulose, methyl cellulose, or inorganic divalent alkali metal hydroxides such as MgOH, can also be used in place of polyvinyl pyrrolidone in this process.

In Example III, macroporous submicron sized particles are produced and polymerization is conducted in the presence of an active ingredient which does not dissolve or swell the resulting polymer. The monomers and the active ingredient are carefully selected so as to be mutually soluble, but insoluble in the aqueous suspending medium. Droplets are formed and polymerization occurs within the suspended droplets resulting in the formation of beads or spheres. The active ingredient is polymerized "in situ" which means that it is entrapped and contained within the beads, but the active ingredient can be released from the bead.

A volatile hydrocarbon solvent or porogenic agent can be substituted for the nonvolatile active ingredient, and then removed leaving an empty porous polymer bead which is free of "in situ" entrapped active materials. Such an empty material has utility as such or the material can be "post adsorbed" again with an active ingredient and used in a loaded form.

Examples of polyunsaturated monomers which may be employed according to any of the preceding examples are ethylene glycol dimethacrylate, triethylene glycol dimethacrylate, tetraethylene glycol dimethacrylate, and propylene, dipropylene and higher propylene glycols; 1,3 butyleneglycol dimethacrylate; 1,4 butanediol dimethacrylate; 1,6 hexanediol dimethacrylate, neopentyl glycol dimethacrylate, hisphenol A dimethacrylate; divinylbenzene and trivinylbenzene; divinyltoluene and trivinyltoluene; triallyl maleate, triallyl phosphate, diallyl maleate, and diallyl itaconate.

Monounsaturated monomers which can be used according to any of the preceding examples are methacrylates and acrylates having straight-chain, branched-chain, or closed rings, with 5 to 30 carbon atoms, and more particularly those containing 5 to 18 carbon atoms. Preferred monomers are lauryl methacrylate, 2-ethylhexyl methacrylate, methylhexyl methacrylate, isodecyl methacrylate, stearyl methacrylate, cyclohexyl methacrylate, and styrene.

Highly crosslinked polymeric systems consisting of particles of submicron size can also be prepared according to the invention from single monomers having at least two polymerizable unsaturated bonds and containing no comonomers having a monounsaturated moiety.

It has been found that entrapped ingredients can be removed mechanically by utilizing an unexpected property of the polymer adsorbent of this invention. The polymer material while being shear sensitive, is surprisingly not compressive sensitive. Thus, it is possible to apply compressive forces generated by a pair of stainless steel surfaces to the laden adsorbent polymer material to squeeze out and remove an entrapped active ingredient. The compressive forces do not cause a degenerative effect upon the resulting adsorbent material.

The silicone conditioner, according to the invention, is an organic polysiloxane most preferably having a viscosity of at least sixty thousand centistokes. Such polysiloxanes have the repeating unit

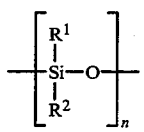

wherein n is an integer having a value greater than 1; $R^1$ is an alkyl radical containing 1 to 7 carbon atoms or a phenyl group; and $R_2$ is hydrogen, an alkyl radical containing 1 to 7 carbon atoms or a phenyl group. Illustrative polysiloxanes encompassed by the above formula are polydimethylsiloxane, polydiethylsiloxane, polymethylethylsiloxane, polymethylphenylsiloxane, polydiphenylsiloxanes, diphenylsilanediol, and blends of two or more of the foregoing siloxanes. Most preferred are polydimethylsiloxane fluids.

In addition to the organic polysiloxanes, the compositions may also include an aminofunctional polysiloxane. The aminofunctional polysiloxane is a silicone fluid with highly polar pendant aminoalkyl modifying groups that enhance the durability of the film formed by the polysiloxanes present and promotes adhesion of the formed film to a wide variety of substrates including hair.

Particularly preferred aminofunctional polysiloxanes include reactive and non-reactive hydrolyzable and non-hydrolyzable derivatives which are wholly, or in part, terminally substituted with aminopropyl, aminobutyl, or diamino pendant chains. Suitable aminofunctional siloxane polymers have the formula:

wherein R' denotes an alkyl group of 1 to 4 carbons or a phenyl group with the proviso that at least 50 percent of the total number of R' groups are methyl; Q denotes an amine functional substituent of the formula —R"Z wherein R" is a divalent alkylene radical of 3 to 6 carbon atoms and Z is a monovalent radical selected from the group consisting of —$NR_2'''$, and —$NR'''(CH_2)_nNR_2'''$; wherein R''' denotes hydrogen or an alkyl group of 1 to 4 carbons, and n is a positive integer having a value of from 2 to 6; z has a value of 0 or 1; x has an average value of 25 to 3000; y has an average value of 0 to 100 when z is 1, y has an average value of .1 to 100 when z is 0; with the proviso that in all cases y has an average value that is not greater than one tenth the average value of x.

Suitable R' groups are represented by and may be independently selected from among methyl, ethyl, propyl, isopropyl, butyl, isobutyl, and phenyl, with the proviso that at least fifty percent of the R' groups are methyl.

The alkylene radicals represented by R" may include trimethylene, tetramethylene, pentamethylene, —$CH_2CHCH_3CH_2$—, and —$CH_2CH_2CHCH_3CH_2$—. Siloxanes where R" is a trimethylene or an alkyl substituted trimethylene radical such as —$CH_2CHCH_3CH_2$—, are preferred.

Alkyl groups of 1 to 4 carbon atoms as represented by R''' include methyl, ethyl, propyl, isopropyl, butyl, and isobutyl.

Useful Z radicals include the unsubstituted amine radical —$NH_2$, alkyl substituted amine radicals such as —$NHCH_3$, —$NHCH_2CH_2CH_2CH_3$, and —$N(CH_2CH_3)_2$; and aminoalkyl substituted amine radicals such as —$NHCH_2CH_2NH_2$, —$NH(CH_2)_6NH_2$, and —$NHCH_2CH_2CH_2N(CH_3)_2$.

When z is zero, the silicone polymer has only pendent amine functional substituents in the polymer chain. When z is one, the silicone polymer may have only terminal amine functional substituents or both terminal and pendent amine functional substituents in the polymer chain. Preferably, x may vary from a value of 25 to 100, and y may vary from zero to 100 when z is one and from one to 100 when z is zero. Most preferably, the value of $x+y$ is in the range of about 50 to 500.

In some instances it may be desirable to deliver to the hair a volatile silicone. The volatile silicone in accordance with the present invention is a low viscosity methylsilicone fluid. The volatile low viscosity methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{\frac{1}{2}}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid, whereby the methylsilicone fluid has a viscosity of less than about one hundred centistokes measured at twenty-five degrees Centigrade.

The volatile low viscosity methylsilicone fluid contains dimethylsiloxane units and optionally trimethylsiloxane units. Preferably, the methylsilicone fluid has a viscosity of less than about ten centistokes. Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and possess viscosities preferably generally less than about ten centistokes measured at twenty-five degrees Centigrade. Most preferably, the viscosity is 0.65 to 5.0 centistokes. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula Me$_3$SiOSiMe$_3$; octamethyltrisiloxane which has a boiling point of 152 degrees Centigrade and the formula Me$_3$SiOMe$_2$SiOSiMe$_3$; hexamethylcyclotrisiloxane which has a boiling point of 133 degrees Centigrade and the formula [(Me$_2$)SiO]$_3$; octamethylcyclotetrasiloxane which has a boiling point of 171 degrees Centigrade and the formula [(Me$_2$)SiO]$_4$; and decamethylcyclopentasiloxane which has a boiling point of 205 degrees Centigrade and the formula [(Me$_2$)SiO]$_5$.

These methylsilicone fluids may be used alone, or as mixtures in combinations of two or more. Mixtures of the methylsilicone fluids will result in a volatile material having an evaporating behavior different from any one of the individual methylsilicone fluids.

The hair shampoo compositions of the present invention contain a surfactant such as an anionic, amphoteric, nonionic, or cationic emulsifying agent, and mixtures of such emulsifying agents. The surfactant should provide an acceptable level of foam on the hair and be capable of cleaning the hair. Most preferred of the emulsifying agents are water soluble anionic surfactants.

Suitable water soluble anionic surfactants include sulfonated and sulfated alkyl, aralkyl, and alkaryl anionic detergents such as alkyl succinates, alkyl sulfosuccinates, and N-alkyl sarcosinates. Representative detergents are the sodium, magnesium, ammonium, and the mono-, di-, and triethanolamine salts of alkyl and aralkyl sulfates, as well as the salts of alkaryl sulfonates. The alkyl groups of the detergents should have a total of from twelve to about twenty-one carbon atoms, and may be unsaturated. Fatty alkyl groups are preferred. The sulfates may be sulfate ethers containing one to ten ethylene oxide or propylene oxide units per molecule, with two to three ethylene oxide units being sufficient for most purposes.

Typical water soluble anionic detergents are sodium lauryl sulfate, sodium lauryl ether sulfate, ammonium lauryl sulfate, triethanolamine lauryl sulfate, sodium C14–16 olefin sulfonate, ammonium C12–15 pareth sulfate, sodium myristyl ether sulfate, ammonium lauryl ether sulfate, disodium monooleamido sulfosuccinate, ammonium lauryl sulfosuccinate, sodium dodecylbenzene sulfonate, triethanolamine dodecylbenzene sulfonate, sodium isothionate, and sodium N-lauryol sarcosinate.

Among the various surfactants classified as amphoteric or ampholytic which may be used are cocoamphocarboxyglycinate, cocoamphocarboxypropionate, cocobetaine, N-cocamidopropyl dimethylglycine, and N-lauryl-N-carboxymethyl-N-(2-hydroxyethyl) ethylenediamine. Other suitable amphoteric detergents which may be used include betaines and sultaines.

Betaines may have the formula R'R"R'"N+(CH$_2$)mCOO− in which R' is an alkyl group having twelve to eighteen carbon atoms and mixtures thereof; R" and R'" are lower alkyl groups of one to three carbon atoms; and m has a value of one to four. Specific compounds may include alpha-(tetradecyldimethylammonio)acetate, beta-(hexadecyldiethylammonio)propionate, and gamma-(dodecyldimethylammonio)butyrate.

Sultaines may have the formula R'R"R'"N+(CH$_2$)$_m$SO$_3$− in which R', R", R'", and m, are the same as defined above. Specific compounds may include 3-(dodecyldimethylammonio)-propane-1-sulfonate, and 3-(tetradecyldimethylammonio)ethane-1-sulfonate.

Nonionic surfactants suitable for use in the hair shampoo compositions of the present invention can be fatty acid alkanolamides and amine oxide surfactants. Representative fatty acid alkanolamides include fatty acid diethanolamides such as isostearic acid diethanolamide, laurie acid diethanolamide, capric acid diethanolamide, coconut fatty acid diethanolamide, linoleic acid diethanolamide, myristic acid diethanolamide, oleic acid diethanolamide, and stearic acid diethanolamide. Suitable fatty acid monoethanolamides include coconut fatty acid monoethanolamide. Fatty acid monoisopropanolamides which may be used are oleic acid monoisopropanolamide and laurie acid monoisopropanolamide.

Amine oxide nonionic surfactants suitable for use in the present invention are N-alkyl amine oxides such as N-cocodimethylamine oxide, N-lauryl dimethylamine oxide, N-myristyl dimethylamine oxide, and N-stearyl dimethylamine oxide. Suitable N-acyl amine oxides are N-cocoamidopropyl dimethylamine oxide and N-tallowamidopropyl dimethylamine oxide. N-alkoxyalkyl amine oxides such as bis(2-hydroxyethyl)C12–15 alkoxy-propylamine oxide may also be employed. The hydrophobic portion of the amine oxide surfactant should be provided by a fatty hydrocarbon chain of about ten to twenty-one carbon atoms.

Cationic surfactants useful in the compositions of the present invention may include those compounds which contain amino or quaternary ammonium hydrophilic moieties in the molecule which are positively charged, such as quaternary ammonium salts. Representative of the various quaternary ammonium salts which may be employed are ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride.

The hair shampoo compositions of the invention may contain other adjuvants to provide a product which is aesthetically pleasant to the consumer such as thickeners, perfumes, colorants, electrolytes, pH control agents, foam boosters and builders, foam stabilizers, antimicrobials, preservatives, antioxidants, ultraviolet light absorbers, pearlescent agents such as ethylene glycol monostearate and ethylene glycol distearate, and medicaments.

Thickeners are used to facilitate the hand application of the composition to the hair, and are added in sufficient quantities to provide a more luxurious effect. Hair care compositions with viscosities in the range of six thousand to twelve thousand centistokes measured at twenty-five degrees Centigrade, are generally sufficient. Representative thickening agents which may be used are sodium alignate; gum arabic; guar gum; hydroxypropyl guar gum; cellulose derivatives such as methylcellulose, hydroxypropyl methylcellulose, hydroxyethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; and derivatives of saccharides such as PEG-120 methyl glucose dioleate.

Only cosmetically acceptable perfumes and fragrances should be used to prepare the composition. Colorants may be added where it is desired to confer a hue to the composition. An acid may be employed to adjust the pH within the range of about five to nine. Any water soluble carboxylic acid or mineral acid may be employed. Suitable compounds include mineral acids such as hydrochloric acid, sulfuric acid, and phosphoric acid; monocarboxylic acids such as acetic acid, lactic acid, and propionic acid; and polycarboxylic acids such as succinic acid, adipic acid, and citric acid.

Other conditioners may be added to the composition in the form of organic cationic conditioning agents for the purpose of providing additional hair grooming. Such cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23.

Cationic surfactants such as cetyl trimethylammonium chloride, cetyl trimethylammonium bromide, and stearyltrimethylammonium chloride, may also be employed in the compositions as a cationic conditioning agent.

A preservative may be required and representative compounds which may be employed include formaldehyde, DMDM hydantoin, 5-bromo-5-nitro-1,3-dioxane, methyl paraben, propyl paraben, sorbic acid, diazolidinyl urea, imidazolidinyl urea, and 5-chloro-2-methyl-4-isothiazolin-3-one which is a product sold under the trademark KATHON® CG by the Rohm & Haas Company, Philadelphia, Pa.

The conditioning shampoos according to the present invention are designed to render the hair easy to comb and tangle free in the wet state, as well as glossy and soft when dry. Such conditioning is provided by the silicone conditioner which upon rinsing produce a thin film on the hair. This film functions as a lubricant when the hair is wet and prevents static charge and "flyaway" when the hair is dry. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving.

Shampoos according to the present invention contain 23 to 90 percent by weight of water; 5 to 70 percent by weight of a surfactant which is one or a mixture of one or more anionic, cationic, nonionic, or amphoteric, emulsifying agents, preferably 5 to 48 percent by weight of an anionic surfactant and 1 to 20 percent by weight of a nonionic surfactant; 2.5 to 3.75 percent by weight of a silicone conditioning agent, preferably 2.5 to 3.35 percent by weight; 1.25 to 2.5 percent by weight of the hydrophobic macroporous polymer which is the carrier for the silicone conditioner, preferably 1.75 to 2.5 percent by weight; zero to 1.0 percent by weight of a suitable preservative, preferably 0.1 to 1.0 percent by weight; zero to 2.0 percent by weight of a suitable thickening agent such as an electrolyte, preferably 0.1 to 1.0 percent by weight; and zero to 1.0 percent by weight of one or more adjuvants such as a fragrance, a pH adjusting agent, a colorant, a foam booster or foam builder, a foam stabilizer, an antioxidant, an ultraviolet light absorber, a pearlescent agent such as ethylene glycol monostearate and ethylene glycol distearate, and a medicament.

The silicone conditioner is added to the shampoo composition entrapped in a nontoxic hydrophobic macroporous highly crosslinked polymer. The polymer is in the form of a mixture of particulates including unit particles, agglomerates, and aggregates. The polymer contains 30 to 75 percent by weight of the silicone conditioner, preferably 50 to 75 percent by weight, most preferably 50 to 65 percent by weight.

The following examples are set forth for the purpose of further illustrating the concepts of the invention in more detail.

EXAMPLE IV

A shampoo composition representative of the present invention was prepared by combining 59.0 percent by weight of water; 33.0 percent by weight of ammonium lauryl sulfate as the anionic surfactant; 2.8 percent by weight of Cocamide DEA as the nonionic surfactant; 0.1 percent by weight of 5-chloro-2-methyl-4-isothiazolin-3-one as the preservative; 0.1 percent by weight of ammonium chloride electrolyte as the thickener; and 5.0 percent by weight of a silicone fluid conditioner entrapped in a nontoxic hydrophobic macroporous highly crosslinked polymer. In its preparation, water and the surfactants were first mixed together with agitation until uniform. The silicone fluid conditioner was added and mixing was continued until uniform. The electrolyte and the preservative were then added, and mixing was continued for a several minutes until a uniform shampoo had been obtained.

In Example IV, the anionic surfactant used was STANDAPOL A, which is a product and tradename of the Henkel Corporation, Cincinnati, Ohio. Cocamide DEA is the CTFA designation for a mixture of ethanolamides of coconut acid. This nonionic surfactant was MONAMID 1159, a product and tradename of Mona Industries Incorporated, Paterson, N.J.

Testing of the shampoo composition was conducted under several different scenarios including "INSTRON COMBING". The procedure for "INSTRON COMBING" is set forth in the following examples.

EXAMPLE V

Dark brown "virgin" European human hair was used for testing the shampoo of Example IV. A master hank of hair about eight inches in length was subdivided into a series of individual hair tresses. Each tress weighed about 2.5 grams. The top one inch portion of the hair tress was trimmed and glued to a 2"×2" plastic tab using DUCO CEMENT®. The cement was allowed to dry, and the hair tress was combed and trimmed to a length which allowed six inches of hair to extend below the bottom of the plastic tab. Each "virgin" tress was rinsed for thirty seconds with forty degree Centigrade tap water. The tress was shampooed and lathered with two milliliters of a fifty percent solution of PRELL® shampoo for sixty seconds by stroking the tress downwardly. The tress was rinsed for sixty seconds with tap water. Excess water was removed from the tress by passing the tress between the index and middle fingers. Instead of employing a commercial brand shampoo for treating the "virgin" tress, there may be substituted a blank shampoo prepared by combining 450 grams of ammonium lauryl sulfate (STANDAPOL A) with 450 grams of distilled water. The tress was hand combed, and evaluated using the INSTRON "WET" and the INSTRON "DRY" COMBING procedures.

EXAMPLE VI

"INSTRON COMBING" is an industry recognized test for determining hair conditioning by the ease of wet combing and the ease of dry combing. The test employs an INSTRON strain gauge which is equipped to measure the force required to comb the hair. Conditioning performance is based on the ability of a particular hair treating formulation such as a shampoo or a hair conditioner to reduce the force required to comb the hair with the INSTRON strain gauge. The force is reported as Average Combing Load (ACL). The lower (ACL) value, the better is the conditioning effect imparted by the formulation being tested. Typically, (ACL) base lines are initially established with "untreated" tresses. The Average Combining Load is defined as the area under the force curve divided by the length or distance traveled by the INSTRON comb. This number is reported in grams or kilograms of force. The effectiveness of a treatment is the percent change in (ACL) after treatment, and this value is calculated as % Change ACL=treated hair ACL−untreated hair ACL×100 %/untreated ACL. An effective treatment is a negative number. A positive number indicates that the hair is more difficult to comb than in its untreated state.

EXAMPLE VII

For tests involving a conditioning shampoo, the hair tress is rinsed with tap water at 40° C. for thirty seconds. The test shampoo is applied to the tress in the amount of 0.5 milliliters, and lathered for thirty seconds by stroking the tress downwardly. The tress is rinsed for thirty seconds with 40° C. tap water, and 0.5 milliliters of the test shampoo are applied to the tress for a second time, and lathered for thirty seconds by stroking the tress downwardly. The tress is rinsed for thirty seconds with 40° C. tap water, and excess water is removed by passing the tress between the index and middle fingers. For tests involving a hair conditioner, the hair tress is rinsed with tap water at 40° C. for thirty seconds. The test conditioner is applied to the tress in the amount of one milliliter, and the tress is stroked for thirty seconds. The tress is rinsed for thirty seconds with 40° C. tap water, and excess water is removed by passing the tress between the index and middle fingers.

EXAMPLE VIII

According to the INSTRON WET COMBING method, each hair tress is soaked for 15-30 minutes in distilled water. Excess water is removed by passing the tress through the index and middle fingers. The tress is untangled by combing the tress by hand three times. The tress is retangled by dipping the tress in distilled water three times, and excess water is removed by passing the tress through the index and middle fingers twice. The tress is placed on a hanger and INSTRON combed. The results of the INSTRON WET COMBING test conducted with the shampoo of the present invention are shown below in Table I.

EXAMPLE IX

According to the INSTRON DRY COMBING method, each hair tress is stored overnight in a constant environment to normalize the water content of the hair. The tress is untangled by combing the tress by hand three times. The tress is retangled by swirling the tress three times clockwise, and three times counterclockwise. The tress is placed on a hanger and INSTRON combed.

TABLE I

| INSTRON WET COMBING | |
|---|---|
| Shampoo Applied | Percent Change (ACL) |
| Control (No Silicone) | 38.8 |
| Silicone Control | 0.5 |
| Silicone Shampoo A | −3.4 |
| Silicone Shampoo B | 7.3 |
| Silicone Shampoo C | −3.8 |
| Silicone Shampoo D* | −27.8 |
| Silicone Shampoo E* | −32.3 |

* = Indicates a Shampoo representative of the invention.

In Table I, the "Control" shampoo was a composition prepared according to Example IV, but omitting the entrapped silicone fluid conditioner. The "Control" shampoo contained no silicone. The "Silicone Control" shampoo was a composition prepared according to Example IV, but omitting the entrapped silicone fluid conditioner, and substituting instead a mechanically prepared nonionic emulsion form of a polydimethylsiloxane fluid having a viscosity of 60,000 centistokes.

The "Silicone Shampoo A" was a composition prepared according to Example IV, and containing an entrapped silicone fluid conditioner. The silicone fluid was a polydimethylsiloxane fluid having a viscosity of 350 centistokes. The silicone fluid conditioner was entrapped in a nontoxic hydrophobic macroporous highly crosslinked polymer. The polymer was in the form of a spherical bead prepared by a process according to Example III. The beads had an average diameter of about twenty microns. The monomers used to prepare the beads were methyl methacrylate and ethylene glycol dimethacrylate. The bead polymer contained 50% by weight of the silicone fluid. "Silicone Shampoo A" is not representative of the present invention, but is a comparative shampoo.

The "Silicone Shampoo B" was a composition prepared according to Example IV, and containing an entrapped silicone fluid conditioner. The silicone fluid was a polydimethylsiloxane fluid having a viscosity of 350 centistokes. The silicone fluid conditioner was entrapped in a nontoxic hydrophobic macroporous highly crosslinked polymer. The polymer was in the form of a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns. The polymer was prepared by a process according to Example I. The polymer contained 50% by weight of the silicone fluid. "Silicone Shampoo B" is not representative of the present invention, but is a comparative shampoo.

The "Silicone Shampoo C" was a composition prepared according to Example IV, and containing an entrapped silicone fluid conditioner. The silicone fluid was a polydimethylsiloxane fluid having a viscosity of 60,000 centistokes. The silicone fluid conditioner was entrapped in a nontoxic hydrophobic macroporous highly crosslinked polymer. The polymer was in the form of a spherical bead prepared by a process according to Example III. The beads had an average diameter of about twenty microns. The monomers used to prepare the beads were methyl methacrylate and ethylene glycol dimethacrylate. The bead polymer contained 50% by weight of the silicone fluid. "Silicone Shampoo C" is not representative of the present invention, but is a comparative shampoo.

The "Silicone Shampoo D" was a composition prepared according to Example IV, and containing an entrapped silicone fluid conditioner. The silicone fluid was a polydimethylsiloxane fluid having a viscosity of 60,000 centistokes. The silicone fluid conditioner was entrapped in a nontoxic hydrophobic macroporous highly crosslinked polymer. The polymer was in the form of a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns. The polymer was prepared by a process according to Example I. The polymer contained 50% by weight of the silicone fluid. "Silicone Shampoo D" is representative of the present invention.

The "Silicone Shampoo E" was a composition prepared according to Example IV, and containing an entrapped silicone fluid conditioner. The silicone fluid was a polydimethylsiloxane fluid having a viscosity of 60,000 centistokes. The silicone fluid conditioner was entrapped in a nontoxic hydrophobic macroporous highly crosslinked polymer. The polymer was in the form of a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns. The polymer was prepared by a process according to Example I. The polymer contained 65% by weight of the silicone fluid. "Silicone Shampoo E" is representative of the present invention.

It can be seen in Table I, that the "Silicone Shampoo D" and the "Silicone Shampoo E" which are representative of the present invention, each achieved a significantly better rating under the INSTRON WET COMBING test; in comparison to the other five compositions tested.

Testing of the shampoo composition was conducted under another different scenario which is set forth in the following example.

EXAMPLE X

Atomic Absorption Spectroscopy (AAS) is a known test method for determining the amount of silicone polymer deposited on the hair. The procedure consists of a solvent extraction and sonification step using methyl isobutyl ketone as the extraction solvent, in which the silicone polymer is desorbed from hair fibers and into the extraction solvent. The resulting solution is then analyzed for silicon content by Atomic Absorption Spectroscopy (AAS). Hair fibers treated with several of the shampoos shown in Table I were further tested according to the AAS procedure, and the results of the AAS tests are shown below in Table II.

TABLE II

| ATOMIC ABSORPTION | |
|---|---|
| Shampoo Applied | Amount Absorbed (ppm) |
| Control (No Silicone) | 0.0 |
| Silicone Control | 0.0 |
| Silicone Shampoo A-1 | 0.0 |
| Silicone Shampoo B | 0.0 |
| Silicone Shampoo C | 0.0 |
| Silicone Shampoo E* | 178.0 |

* = Indicates a Shampoo representative of the invention.

In Table II, the "Silicone Shampoo A-1" was the same as the "Silicone Shampoo A" in Table I, except that the polymer beads had an average diameter of about nine microns instead of twenty microns.

Table II clearly reveals the dramatic improvement which can be achieved with "Silicone Shampoo E", which is a composition representative of the present invention. Again, "Silicone Shampoo E" contained a polydimethylsiloxane fluid with a viscosity of 60,000 centistokes entrapped in a hydrophobic macroporous highly crosslinked polymer in the form of a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns. The polymer was prepared by a process according to Example I and contained 65% by weight of the silicone fluid.

Testing of the shampoo composition was conducted under yet another different scenario which is set forth in the following example.

EXAMPLE XI

A panel test was used to generate subjective hair combing and feel data. The test was basically a repetition of the procedure followed above in Examples V to IX, but the testing was conducted by volunteer panelists who were asked to evaluate tresses with regular combs instead of an INSTRON STRAIN GAGE. The panelists consistently reported, that in comparison to the other shampoos shown in Tables I and II, that "Silicone Shampoo D" and "Silicone Shampoo E" which are representative of the present invention, each were excellent in their ratings of wet and dry combing, and had a softer feel.

The entrapment feature of the present invention can be utilized in other applications relating to the treatment or the care of hair. Thus, fragrances, colognes, and perfumes, can be entrapped in the macroporous polymer particulate, in order to mask their effect for subsequent release over time. Gloss enhancement and slip agents can be entrapped and delivered during the perming of hair or during its wet combing.

Various hair care additives may be delivered to the hair which are otherwise not compatible with the formulation, adversely effect its stability, or cause deactivation, such as the addition to water based fixative products of non-aqueous soluble resins, or in the slow release of water-soluble dyes and colorants. Dry powders can be applied to the hair by entrapment in the macroporous polymer particulate, and subsequently activated by rubbing the particulate into the scalp. Actives effective in the control of dandruff or sebum can be entrapped and delivered to the hair, as well as actives useful in cuticle coat products. Where a visual effect is desirable, the macroporous polymer particulate can be suspended in clear liquid systems.

As noted above, especially good results are obtained with silicones having a viscosity of at least sixty thousand Centistokes. However, the general concept of the invention may be applied in the delivery of any polysiloxane having a viscosity in the range of 0.65 to as high as several million centistokes. In addition, mixtures of polysiloxanes having higher and lower viscosities can be entrapped and delivered to hair.

Other variations and modifications may be made in the compounds, compositions, and methods described herein, without departing from the essential features and concepts of the present invention.

The forms of the invention described herein are exemplary only and are not intended as limitations on the scope of the invention as defined in the appended claims.

That which is claimed is:

1. A method of depositing a silicone conditioner to hair comprising delivering the silicone conditioner to the hair as an ingredient of an aqueous shampoo containing 23-90 percent by weight of water, 5-48 percent by weight of an anionic surfactant, 1-20 percent by weight of a nonionic surfactant, 2.5-3.75 percent by weight of the silicone conditioner and 1.25 to 2.5 percent of a hydrophobic macroporous crosslinked polymethacrylate polymer, the silicone conditioner being a polydimethylsiloxane fluid having a viscosity of at least sixty thousand centistokes, the polydimethylsiloxane fluid being entrapped in said hydrophobic macroporous crosslinked polymethacrylate polymer, the macroporous polymer being in the form of a mixture of particulates including unit particles having an average diameter of less than one micron; agglomerates formed of fused unit particles and having an average diameter of about twenty to eighty microns; and aggregates formed of clusters of fused agglomerates and having an average diameter of two-hundred to twelve-hundred microns; the nontoxic hydrophobic macroporous crosslinked polymer containing 30-75 percent by weight of the polydimethylsiloxane fluid conditioner.

2. A method according to claim 1 in which the hydrophobic macroporous crosslinked polymer contains 50-65 percent by weight of the polydimethylsiloxane fluid conditioner.

* * * * *